US010874835B2

(12) United States Patent
Rosenberg et al.

(10) Patent No.: US 10,874,835 B2
(45) Date of Patent: Dec. 29, 2020

(54) SYSTEMS AND METHODS FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 28 days.

(21) Appl. No.: 16/425,598

(22) Filed: May 29, 2019

(65) Prior Publication Data

US 2019/0275299 A1 Sep. 12, 2019

Related U.S. Application Data

(63) Continuation of application No. 15/911,280, filed on Mar. 5, 2018, now Pat. No. 10,342,954, which is a continuation of application No. 15/066,056, filed on Mar. 10, 2016, now Pat. No. 9,907,934, which is a continuation of application No. 13/649,688, filed on Oct. 11, 2012, now Pat. No. 9,314,596.

(51) Int. Cl.
*A61M 25/04* (2006.01)
*A61M 25/02* (2006.01)

(52) U.S. Cl.
CPC ............ *A61M 25/04* (2013.01); *A61M 25/02* (2013.01); *A61M 2025/028* (2013.01); *A61M 2025/0286* (2013.01)

(58) Field of Classification Search
CPC .................. A61M 25/02; A61M 25/04; A61M 2025/0213; A61M 2025/0233; A61M 2025/024; A61M 2025/0246; A61M 2025/0253; A61M 2025/026; A61M 2025/0266; A61M 2025/0273
See application file for complete search history.

(56) References Cited

U.S. PATENT DOCUMENTS

| 2,525,398 | A | 10/1950 | Collins |
| 3,039,468 | A | 6/1962 | Price |
| 3,059,645 | A | 10/1962 | Hasbrouck et al. |
| 3,108,595 | A | 10/1963 | Overment |
| 3,176,690 | A | 4/1965 | Doubler |
| 3,308,819 | A | 3/1967 | Arp |
| 3,630,195 | A | 12/1971 | Santomieri |
| 3,677,250 | A | 7/1972 | Thomas |

(Continued)

FOREIGN PATENT DOCUMENTS

| WO | WO 1991015254 | 10/1991 |
| WO | WO 2004026152 | 4/2004 |

(Continued)

OTHER PUBLICATIONS

Johnson & Johnson web page printout, "The EndoANCHOR Comparative Summary," printed Sep. 13, 2005, 2 pages.

(Continued)

*Primary Examiner* — Kami A Bosworth
*Assistant Examiner* — Leah J Swanson
(74) *Attorney, Agent, or Firm* — Fish & Richardson P.C.

(57) ABSTRACT

Some embodiments of a medical device anchor system include an anchor device that secures a medical instrument (such as a catheter or the like) in place relative to a skin penetration point using subcutaneous anchors.

20 Claims, 9 Drawing Sheets

(56) References Cited

U.S. PATENT DOCUMENTS

| | | |
|---|---|---|
| 3,717,151 A | 2/1973 | Collett |
| 3,765,032 A | 10/1973 | Palma |
| 3,825,010 A | 7/1974 | McDonald |
| 3,834,380 A | 9/1974 | Boyd |
| 3,856,009 A | 12/1974 | Winnie |
| 3,896,527 A | 7/1975 | Miller |
| 3,938,529 A | 2/1976 | Gibbons |
| 4,043,346 A | 8/1977 | Mobley |
| 4,114,618 A | 9/1978 | Vargas |
| 4,164,943 A | 8/1979 | Hill |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins |
| 4,804,359 A | 2/1989 | Grunwald |
| 4,813,930 A | 3/1989 | Elliott |
| 4,936,823 A | 6/1990 | Colvin |
| 4,986,810 A | 1/1991 | Semrad |
| 5,041,085 A | 8/1991 | Osborne |
| 5,067,957 A | 11/1991 | Jervis |
| 5,122,122 A | 6/1992 | Allgood |
| 5,144,942 A | 9/1992 | Decarie |
| 5,190,546 A | 3/1993 | Jervis |
| 5,256,146 A | 10/1993 | Ensminger |
| 5,267,960 A | 12/1993 | Hayman |
| 5,279,564 A | 1/1994 | Taylor |
| 5,312,337 A | 5/1994 | Flaherty |
| 5,344,439 A | 9/1994 | Otten |
| 5,368,017 A | 11/1994 | Sorenson |
| 5,378,239 A | 1/1995 | Termin |
| 5,456,671 A | 10/1995 | Bierman |
| 5,496,277 A | 3/1996 | Termin |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl |
| 5,693,032 A | 12/1997 | Bierman |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones |
| 5,769,821 A | 6/1998 | Abrahamson |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick |
| 5,921,965 A | 7/1999 | Blei |
| 5,928,266 A | 7/1999 | Kontos |
| 5,944,732 A | 8/1999 | Raulerson |
| 5,947,931 A | 9/1999 | Bierman |
| 5,971,960 A | 10/1999 | Flom |
| 5,989,265 A | 11/1999 | De La Joliniere |
| 6,213,979 B1 | 4/2001 | Bierman |
| 6,231,548 B1 | 5/2001 | Bassett |
| 6,290,676 B1 | 9/2001 | Bierman |
| 6,413,240 B1 | 7/2002 | Bierman |
| 6,447,485 B2 | 9/2002 | Bierman |
| 6,540,693 B2 | 4/2003 | Burbank |
| 6,572,588 B1 | 6/2003 | Bierman |
| 6,582,388 B1 | 6/2003 | Coleman |
| 6,582,403 B1 | 6/2003 | Bierman |
| 6,663,600 B2 | 12/2003 | Bierman |
| 6,679,851 B2 | 1/2004 | Burbank |
| 6,695,861 B1 | 2/2004 | Rosenberg |
| 6,770,055 B2 | 8/2004 | Bierman |
| 6,896,665 B2 | 5/2005 | Picha |
| 6,958,044 B2 | 10/2005 | Burbank |
| 7,056,286 B2 | 6/2006 | Ravenscroft |
| 7,261,708 B2 | 8/2007 | Raulerson |
| D615,649 S | 5/2010 | Zinn |
| 8,235,948 B2 | 8/2012 | Rosenberg |
| 9,314,596 B2 | 4/2016 | Rosenberg |
| 9,907,934 B2 | 3/2018 | Rosenberg |
| 10,342,954 B2 | 7/2019 | Rosenberg |
| 2001/0039399 A1 | 11/2001 | Bierman |
| 2001/0056261 A1 | 12/2001 | Lerman |
| 2002/0068898 A1 | 6/2002 | McGucklin, Jr. |
| 2002/0068899 A1 | 6/2002 | McGucklin, Jr. |
| 2002/0120250 A1 | 8/2002 | Altman |
| 2002/0165489 A1 | 11/2002 | McGucklin, Jr. |
| 2004/0243103 A1 | 12/2004 | King |
| 2005/0043685 A1 | 2/2005 | Schinkel-Fleitmann |
| 2005/0187578 A1 | 8/2005 | Rosenberg |
| 2005/0256458 A1 | 11/2005 | Howard |
| 2005/0273058 A1 | 12/2005 | Bierman |
| 2007/0225651 A1 | 9/2007 | Rosenberg |
| 2007/0265572 A1 | 11/2007 | Smith |
| 2008/0312599 A1 | 12/2008 | Rosenberg |
| 2009/0099527 A1 | 4/2009 | Rosenberg |
| 2009/0326473 A1 | 12/2009 | Rosenberg |
| 2010/0016801 A1 | 1/2010 | Rosenberg |
| 2010/0100049 A1 | 4/2010 | Godfrey |
| 2010/0204656 A1 | 8/2010 | Rosenberg |
| 2010/0324491 A1 | 12/2010 | Bierman |
| 2012/0078191 A1 | 3/2012 | Rosenberg |
| 2014/0107584 A1 | 4/2014 | Rosenberg |
| 2016/0184554 A1 | 6/2016 | Rosenberg |
| 2018/0193604 A1 | 7/2018 | Rosenberg |

FOREIGN PATENT DOCUMENTS

| | | |
|---|---|---|
| WO | WO 2005039419 | 5/2005 |
| WO | WO 2005102438 | 11/2005 |
| WO | WO 2008051810 | 5/2008 |
| WO | WO 2010049735 | 5/2010 |

OTHER PUBLICATIONS

Johnson & Johnson web page printout, "The EndoANCHOR Features and Benefits," printed Sep. 13, 2005, 2 pages.
Johnson & Johnson web page printout, "The EndoANCHOR Firing Sequences," printed Sep. 13, 2005, 2 pages.
PCT International Preliminary Report on Patentability in Appln. No. PCT/US2013/064350, dated Apr. 14, 2015, 18 pages.
PCT International Search Report and Written Opinion in Appln. No. PCT/US2013/064350, dated Jan. 22, 2014, 20 pages.
Web Page Printout of Statlock Device, believed to be publicly available prior to Oct. 11, 2012, 2 pages.

SYSTEMS AND METHODS FOR ANCHORING MEDICAL DEVICES

CLAIM OF PRIORITY

This application is a continuation and claims priority to U.S. patent application Ser. No. 15/911,280, filed on Mar. 5, 2018, which is a continuation of U.S. patent application Ser. No. 15/066,056, filed on Mar. 10, 2016 (now U.S. Pat. No. 9,907,934, issued Mar. 6, 2018), which is a continuation of U.S. patent application Ser. No. 13/649,688, filed on Oct. 11, 2012 (now U.S. Pat. No. 9,314,596, issued Apr. 19, 2016), the entire contents of which are hereby incorporated by reference.

TECHNICAL FIELD

This document relates to devices, systems, and methods for securing the position of a catheter or another medical instrument, for example, at a skin opening.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Alternatively, catheters can contain electrical leads for neuro-stimulation, cardiac pacing, and the like. Following introduction into the patient, the catheter is secured to the patient. In many instances, the catheter is commonly secured to the patient using an adhesive tape on the skin or by suturing a catheter hub to the patient's skin. In other circumstances, the catheter may be secured to the patient using a subcutaneous anchor mechanism (such as an anchor sleeve equipped with anchors that are deployed using an external actuator handle or a separate delivery device). In many cases, the medical practitioner will make efforts to clean the skin area around the catheter insertion site for purposes of a patient's comfort, safety, and improved visualization of the catheter insertion site after the catheter is installed.

SUMMARY

Some embodiments of a medical device anchor system include an anchor device that receives a medical instrument (such as a catheter or the like that is optionally equipped with suture wings) and secures the instrument in place relative to a skin penetration point. For example, the medical anchor device can be configured to releasably mate the suture wings on a hub of a catheter while also providing subcutaneous anchor mechanisms deployable through the skin penetration point that is already occupied by the catheter, thereby reducing or eliminating the need for installing sutures through the suture wings and the patient's skin. Optionally, in some embodiments the anchor device can be adjusted to a folded configuration that aligns the tines of the subcutaneous anchors in a generally side-by-side configuration to facilitate insertion of the anchors through the skin penetration point. Such a configuration may allow the anchor device to be installed after medical instrument is already in place without the need for a second penetration point for the anchor device. In particular embodiments, the anchor device may be configured to simplify the use of the anchor device, make the anchor device more adaptable to use with medical instruments of different sizes, and to facilitate the maintenance and cleaning of the skin tissue at and around the skin penetration point.

Some embodiments described herein include an anchor device for securing the position of a medical instrument. The anchor device may include a retainer body and first and second anchors extending from the retainer body. Optionally, the retainer bodily may includes a first body portion that is pivotably coupled to a second body portion about a longitudinal fold axis. Also, the retainer body may optionally include one or more anchor engagement portions that are configured to releasably receive one or more corresponding apertures defined by a hub of a catheter. The first and second anchors may optionally extend distally from a distal end of the retainer body. Each anchor may include a flexible tine that is deployable in a subcutaneous region to secure the retainer body relative to a penetration point. The first anchor may be coupled to the first body portion and the second anchor may be coupled to the second body portion. Optionally the first body portion of the retainer body may be pivotable relative to the second body portion about the longitudinal fold axis so that the first and second anchors are adjustable from a first configuration in which the flexible tines extend outwardly away from one another to a second configuration in which the flexible tines extend generally in the same direction.

Particular embodiments described herein include an anchor device for securing the position of a medical instrument. The anchor device may include a retainer body comprising a first body portion that is pivotably coupled to a second body portion about a longitudinal fold axis. The retainer body may also include one or more anchor engagement portions being configured to mate with an external structure of a medical instrument to releasably secure the medical instrument to the retainer body. The anchor device may further include first and second anchors that extend distally from a distal end of the retainer body. Each anchor comprising a flexible tine that is deployable in a subcutaneous region to secure the retainer body relative to a penetration point. The first anchor may be coupled to the first body portion, and the second anchor may be coupled to the second body portion. The first body portion of the retainer body may be pivotable relative to the second body portion about the longitudinal fold axis so that the first and second anchors can be adjusted from a first configuration in which the flexible tines extend outwardly away from one another to a second configuration in which the flexible tines extend generally in the same direction.

Further embodiments described herein include a system for securing the position of a medical instrument. The system may include an adapter and an anchor device. The adapter may include a hub portion that is elastically deformable and configured to substantially surround and releasably engage with the outer surface of medical instrument. The adapter may also include a second portion having one or more engagement members extending outwardly from the hub portion. The anchor device may include a retainer body comprising a first body portion that is pivotably coupled to a second body portion. The anchor device may also include one or more anchor engagement portions being configured to releasably couple with the one or more engagement members extending outwardly from the hub portion of the adapter. The anchor device may further include first and second anchors that extend distally from a distal end of the retainer body. Each anchor may include a flexible time that is deployable in a subcutaneous region to secure the retainer bod relative to a penetration point. The first anchor may be coupled to the first body portion, and the second anchor may be coupled to the second body portion. The first body portion of the retainer body may be pivotable relative to the second body portion so that the first and second anchors are adjustable from one another to a removal configuration in which the flexible tines extend generally in the same direction.

Some other embodiments described herein may include a kit of components for securing the position of a catheter relative to a penetration point. The kit may include a sterile package containing two or more adapters having a hub portion with differently shaped or sized longitudinal lumens. Each of the two or more adapters in the sterile package may comprise an elastically deformable material to permit access to the respective longitudinal lumen. Also, each of the two or more adapters in the sterile package may include a one or more flanges extending outwardly away from the hub portion. The hub portion may include a longitudinal slit through a wall portion to permit access to the respective longitudinal lumen. The one or more flanges may each include an adapter engagement portion configured to releasably engage with retention posts of an anchor device.

Additional embodiments described herein may include a kit of components including a sterile package containing an anchor device and a catheter. The catheter may include a hub having one or more apertures configured to releasably mate with the anchor device. The anchor device may include a retainer body including a first body portion that is pivotably coupled to a second body portion. The retainer body may also include one or more anchor engagement portions being configured to releasably couple with one or more corresponding catheter engagement portions on a hub of the catheter. The anchor device may further include first and second anchors that extend distally from the retainer body. Each anchor may include a flexible time that is deployable in a subcutaneous region to secure the retainer bod relative to a penetration point. The first anchor may be coupled to the first body portion, and the second anchor may be coupled to the second body portion. The first body portion of the retainer body may be pivotable relative to the second body portion so that the first and second anchors are adjustable from one another to a removal configuration in which the flexible tines extend generally in the same direction.

Particular embodiments described herein may include a method of using a medical anchor system. The method may include advancing an anchor device toward a skin penetration point while the anchor device is in a folded condition so that a plurality of subcutaneous tines of the anchor device are generally adjacent to each other and oriented to extend in substantially the same direction. The method may also include inserting the subcutaneous tines through the skin penetration point and into a subcutaneous region adjacent to an underside of a skin layer while the anchor device is in the folded condition. Each of the subcutaneous tines may have a shape (optionally, a curved shape) which terminates at a tip of a free end during insertion through the skin penetration point. The method may further include adjusting the anchor device to a non-folded condition after the subcutaneous tines are inserted into the subcutaneous layer so that subcutaneous tines are in an anchored position in which the free ends of the subcutaneous tines extend generally away from one another. The method may include securing a medical instrument to the anchor device after the subcutaneous tines are adjusted to the anchored position in the subcutaneous region. The securing operation may include coupling one or more protrusions extending from the anchor device with one or more apertures located on the medical instrument.

These and other embodiments may provide one or more of the following advantages. First, some embodiments of an anchor system can retain a medical instrument in a desired position relative to a skin penetration point without necessarily requiring sutures or skin adhesives. Second, particular embodiments of the anchor device may be readily adaptable to use with catheters or other medical instruments of different sizes, while also securing the catheter or medical instrument to a skin penetration point in a manner that facilitates improved inspection and cleaning of the skin tissue at and around the skin penetration point. For example, some of these particular embodiments of the anchor device can provide a capless design in which the anchor device releasably couples with an external portion of the catheter or medical device without the need for an attachable cap device, thereby simplifying the process for a practitioner to inspect and clean the anchor device and the skin surface near the skin penetration point. Third, in some embodiments, the anchor device may be adjusted between a folded configuration and a non-folded configuration so that the subcutaneous anchors are arranged side-by-side and extend in generally the same direction during both installation through and removal from the skin penetration point. Fourth, in some embodiments, the anchor device can be installed in accordance with a technique that reduces or eliminates the need to shift the subcutaneous anchors tines to or from a flexed or stressed configuration. Thus, in these embodiments, the subcutaneous anchors may be readily installed and removed from the skin penetration without the need for a separate external actuator or delivery device. Fourth, in some embodiments, the configuration of the anchor device can simplify the process of installing a medical instrument onto the anchor device. Sixth, in some embodiments, the anchor device can be configured to be usable with a variety of styles and sizes of medical instruments. Seventh, in some embodiments, the anchor device can enable a hub of a catheter or other medical instrument to be positioned in close proximity to the skin penetration point.

The details of one or more embodiments of the invention are set forth in the accompanying drawings and the description below. Other features, objects, and advantages of the invention will be apparent from the description and drawings, and from the claims.

DETAILED DESCRIPTION OF ILLUSTRATIVE EMBODIMENTS

Figure 1:
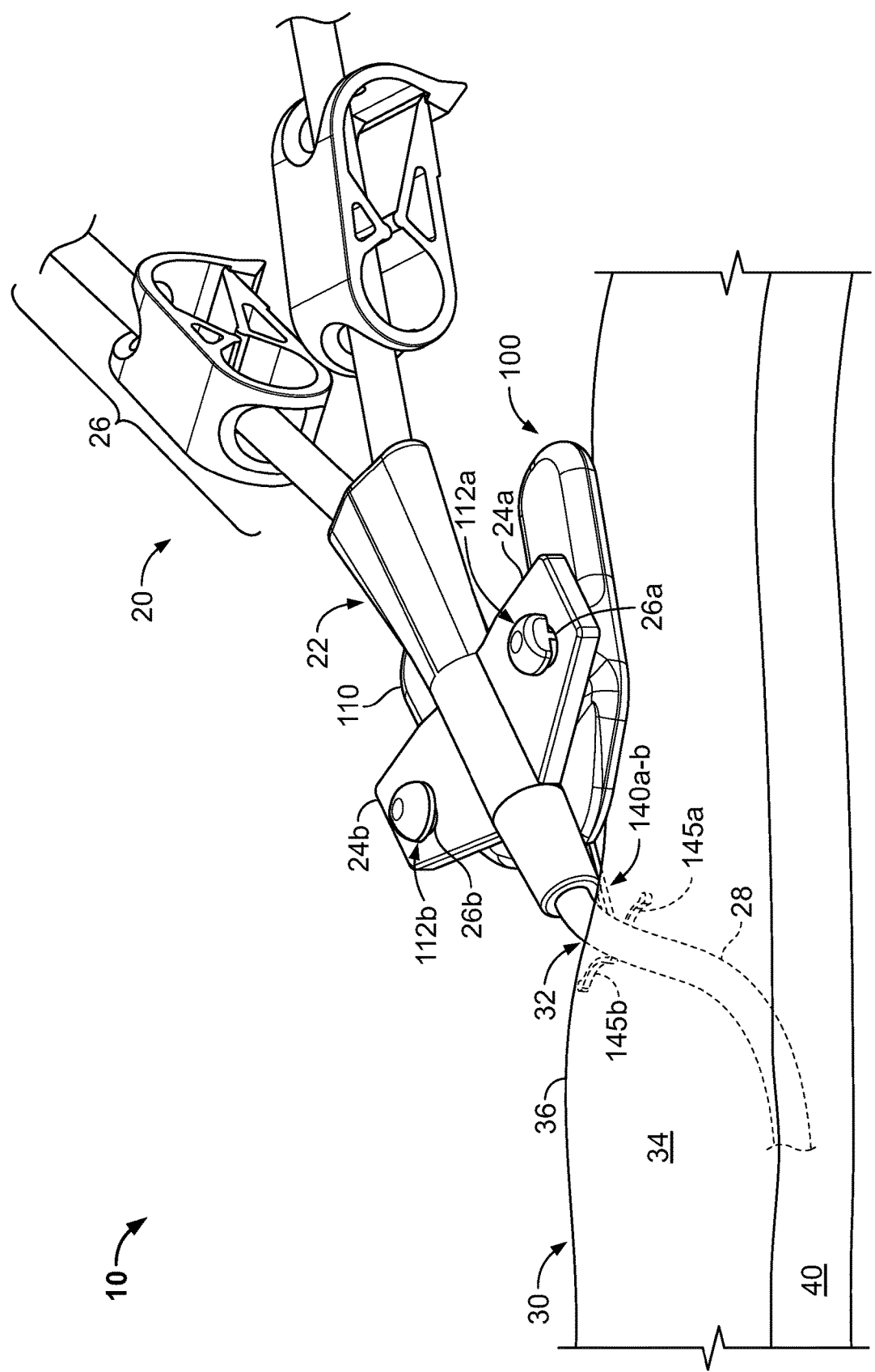
FIG. 1 is a perspective view of an anchor device with a portion of the device located in a subcutaneous region, in accordance with some embodiments.

Referring to FIG. 1, some embodiments of a medical device anchor system 10 include an anchor device 100 that releasably retains a medical instrument 20 in an operative position relative to a portion of skin 30. The medical instrument 20 can be mechanically coupled to the anchor device 100. The anchor device 100, in turn, can be coupled to the portion of skin 30. In this manner, the anchor device 100 can act as an intermediary member to cause the retention of the medical instrument 20 in a desired position with respect to the skin 30. The example embodiment of FIG. 1, can include a central venous catheter 20 inserted through a percutaneous opening formed in the skin (e.g., penetration point 32), proceeding to the underside of the skin 30, and into a vein 40 to provide vascular access for delivering medications, withdrawing fluids, or providing minimally invasive access into a patient.

In this example, the anchor device 100 can generally include a retainer body 110 and one or more anchors 140a-b that extend distally from a distal end of the retainer body 110. As described further below, the retainer body 110 can be configured to couple with the medical instrument 20. The one or more anchors 140a-b can be configured for deployment through a skin penetration point 32 and into in a subcutaneous layer 34, so as to releasably retain the anchor device 100 with respect to the skin 30. For example, the retainer body 110 can include the one or more anchors 140a and 140b that extend distally from the retainer body 110 so as to penetrate through the same skin penetration point 32 as the medical instrument 20 while the retainer body 110 remains external to the skin penetration point. In some embodiments, the skin penetration point 32 may be defined by a small incision, a puncture, or the like through the dermal layers 36.

The anchors 140a-b can include subcutaneous tines 145a-b that, after insertion, reside in a subcutaneous region 34 (e.g., a region immediately under the skin 30 that may comprise a fatty tissue layer) so as to secure the position of the anchor device—and the medical instrument 20 retained therein—relative to the penetration point 32. When the tines 145a-b are deployed in the subcutaneous region 34, the anchor device 100 can be secured to the patient without the retainer body 110 penetrating through the dermal layers 36 of the patient, and without necessarily requiring sutures or adhesive tapes bonded to the skin 30.

As described in more detail below in connection with FIGS. 4-6B, the anchor device 100 can be installed into a skin penetration point 32 in accordance with a technique that reduces or eliminates the need to shift the subcutaneous anchors tines 145a-b of the anchors 140a-b to or from a flexed or stressed configuration. As such, the anchor tines 145a-b need not undergo substantial flexing during installation or removal. In these circumstances, the subcutaneous anchors may be both installed and removed from the skin penetration point 32 advantageously without the need for an external actuator handle or delivery device to deploy the subcutaneous tines 145a-b.

Still referring to FIG. 1, after installation of the subcutaneous anchor tines 145a-b into the subcutaneous layer 34, the retainer body 110 can receive the medical instrument 20. In this example, the medical instrument 20 is embodied as a catheter. Hence, hereinafter the medical instrument 20 may alternatively be referred to as catheter 20, without limiting the medical instrument 20 to such an embodiment. Furthermore, in some embodiments, the anchor device 100 can provide a capless design in which the anchor device 100 releasably couples with an external portion of the catheter 20 without the need for attaching a cap onto the retainer body 110, thereby simplifying the process inspecting and cleaning the anchor device 100 and the skin surface near the skin penetration point 32 after installation.

In this embodiment, the example catheter 20 generally includes a proximal portion 26, a hub 22, and a distal portion 28. The hub 22 can interconnect the proximal portion 26 with the distal portion 28. In some embodiments, the proximal portion 26 of the catheter 20 may have multiple lumens that are suited to deliver multiple types of solutions to the patient. In some such embodiments, the hub 22 can receive the multiple lumens on the proximal end of the hub 22, and merge the multiple lumens so as to connect with a single lumen distal portion 28. For example, as shown in FIG. 1, the proximal portion 26 is depicted as having two lumens, and the distal portion 28 as having a single lumen that is adapted for percutaneous insertion through skin penetration point 32. Hence, the hub 22 can serve the purpose of merging multiple proximal supply lumens into a single distal delivery lumen suited for insertion into the patient.

The hub 22 can further be arranged to couple the catheter 20 onto the anchor device 100. In some embodiments, the hub 22 can include wings 24a-b. The wings 24a-b can have features that facilitate the coupling of the hub 22 to the anchor device 100. For example, some embodiments of the hub 22 can include apertures 26a-b in the wings 24a-b. The apertures 26a-b can be located and sized to couple with corresponding features of the anchor device 100 (e.g., retention posts 112a-b as further described in reference to FIGS. 2A-C). In addition, the hub 22 can be manufactured from an elastomeric or otherwise flexible material, such as silicone or another biocompatible polymer material (e.g., PVC, polypropylene, polystyrene, or the like). In some embodiments, the hub 22 can be made from a combination of materials. For example, at least wings 24a-b may comprise silicone or another flexible biocompatible material so that the wings 24a-b and the apertures 26a-b can flexibly adjust to couple with the retention posts 112a-b of the anchor device 100, whereas the portions of the hub 22 other than the wings 24a-b may comprise a more rigid polymer material. As will be described further in reference to FIGS. 5 and 6B, such flexibility of the wings 24a-b can assist the user in coupling the hub 22 to the anchor device 100 as it relates to aligning the apertures 26a-b with the retention posts 112a-b, and forcing the apertures 26a-b over the mushroom-shaped heads of the retention posts 112a-b. Such flexibility of the wings 24a-b similarly assists with decoupling the hub 22 from the anchor device 100.

Figure 2A:
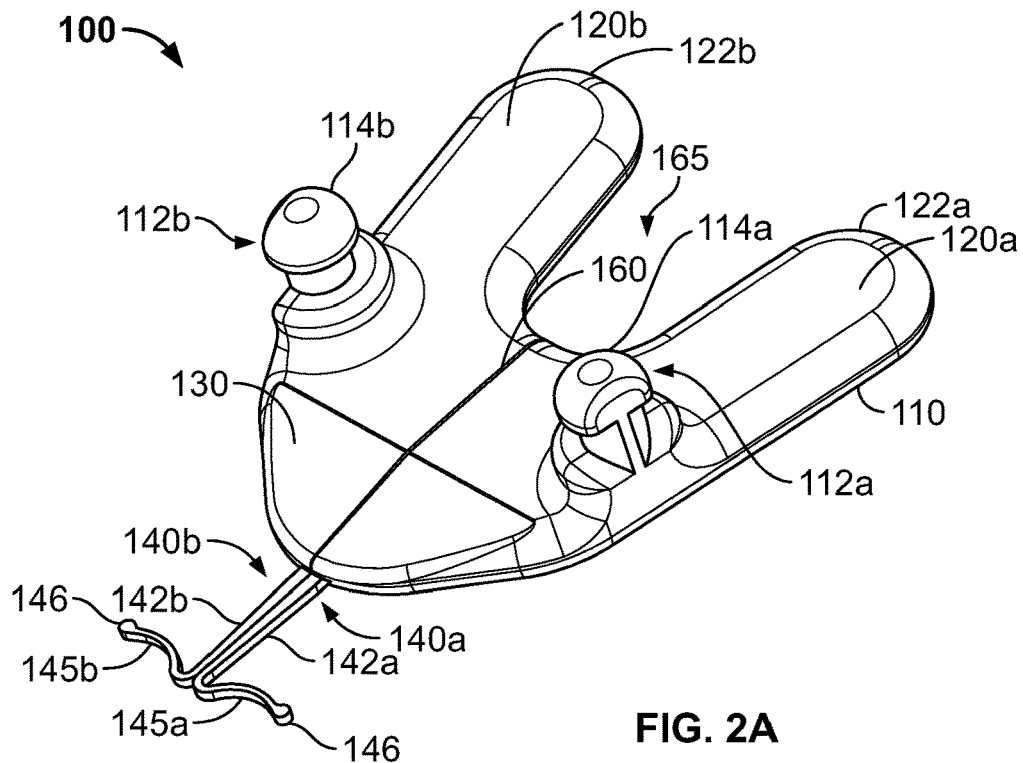
FIGS. 2A-2C are perspective, side, and rear views, respectively, of the anchor device of FIG. 1.
Figure 2B:
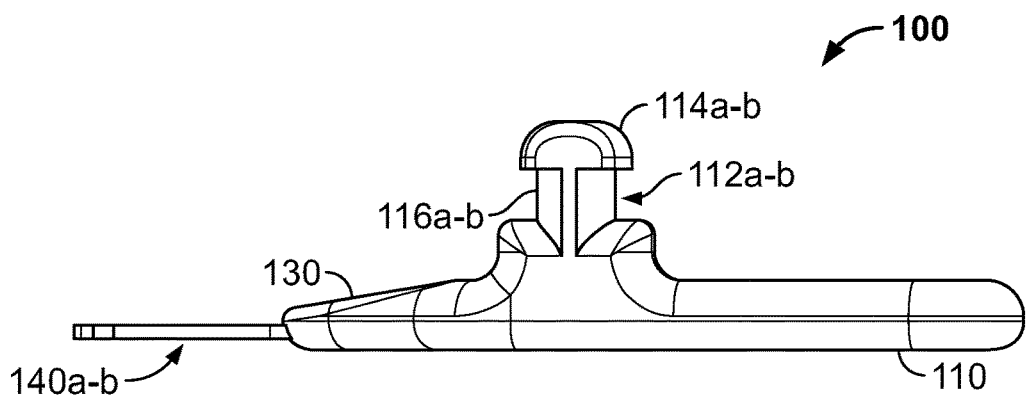
Figure 3A:
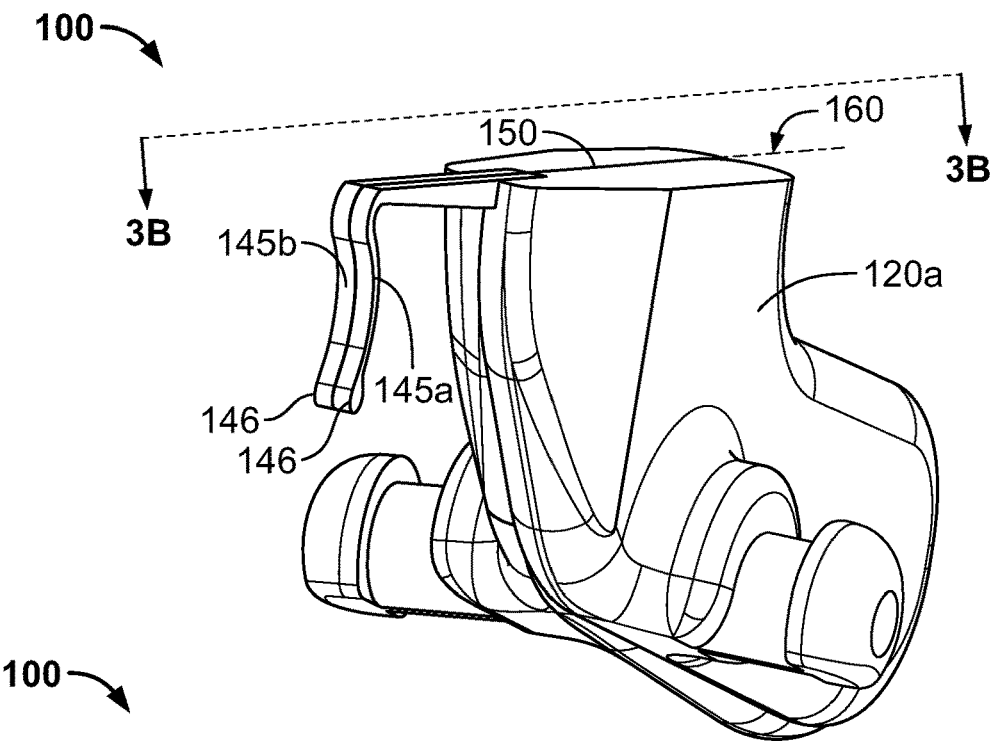
FIGS. 3A-3B are a perspective and top view, respectively, of the anchor device of FIG. 1 in a folded condition, in accordance with some embodiments.
Figure 3B:
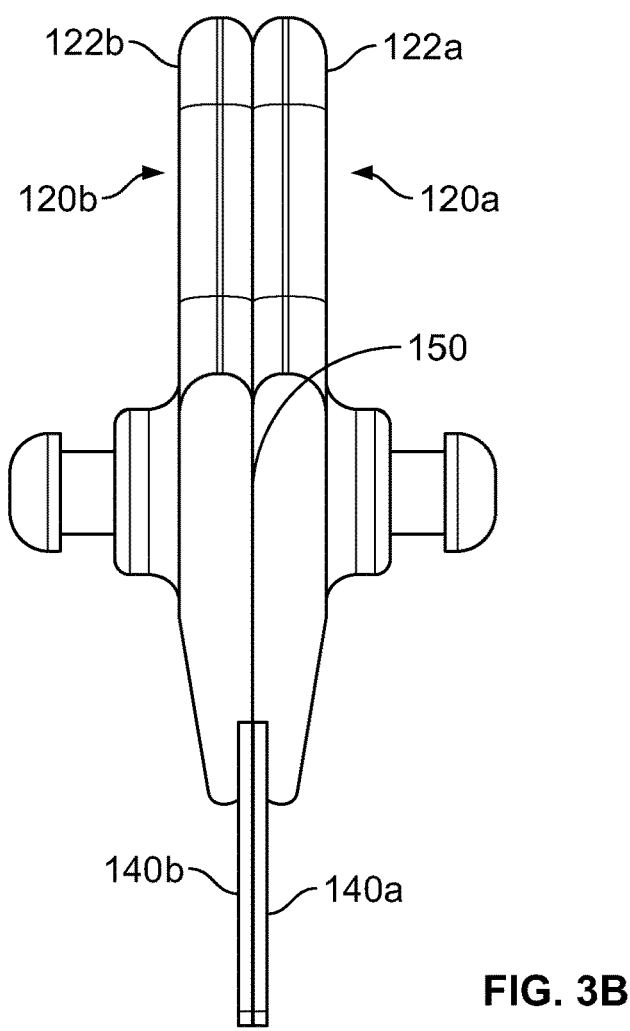

Referring now to FIGS. 2A-2B, some embodiments of the anchor device 100 include the retainer body 110 and the anchors 140a-b, which are connected to and extend distally from the distal end of the retainer body 110. For example, the anchors 140a and 140b can be connected to the retainer body 110 using an over-molding process to secure the anchors 140a-b relative to the retainer body 110. It should also be understood that there exist many manufacturing processes that can secure the anchors 140a and 140b to the retainer body 110. In some embodiments, the retainer body 110 and the anchors 140a and 140b can be manufactured as a single, unitary piece.

in particular embodiments, the anchor device 100 can be configured to be folded longitudinally about a longitudinal fold axis 160 (e.g., a longitudinally extending region configured for enabling the retainer body 110 to repeatedly adjust from a first position to a second, folded position as shown, for example, in FIGS. 3A-3B). Consequently, the retainer body 110 can be described as having a first retainer body portion 120a and a second retainer body portion 120b. In some embodiments, the first and second retainer body portions 120a-b can be substantially mirror images of each other. In alternative embodiments, the first and second portions of the anchor device 100 can be asymmetrical.

Preferably, at least a portion of each anchor 140a-b comprises a flexible material. In some embodiments, the anchors 140a-b may comprise a material that exhibits superelasticity. In some embodiments, at least a portion of the anchors 140a-b (including the tines 145a-b) may be formed from a length of nitinol wire or from a sheet of nitinol material. Alternatively, the anchors 140a-b may comprise a metal material such as stainless steel (e.g., 304 stainless, 316 stainless, custom 465 stainless, and the like), spring steel, titanium, MP35N, and other cobalt alloys, or the like. In another alternative, the anchors 140a-b may be formed from a resilient polymer material. In some embodiments, the anchors 140a-b can be formed from a material or materials that allow the tines 145a-b to be flexed and can resiliently return to an unstressed position.

Figure 2C:
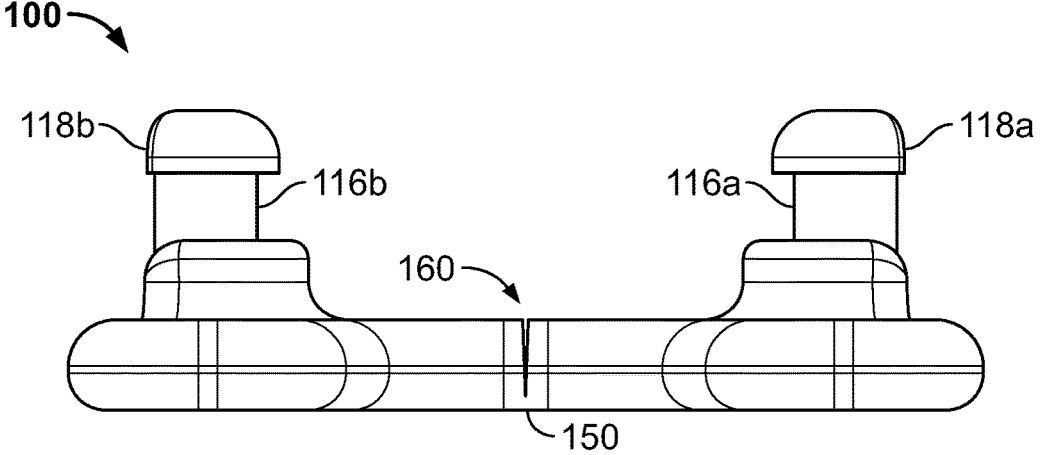

In the embodiment depicted in FIGS. 2A-C, each of the anchors 140a-b may be designed such that the tines 145a-b have an unstressed position wherein the tines 145a-b have a convex curvature. The convex curvature shape of the tines 145a-b may permit the tines 145a-b to abut against the underside of the dermal layers 36 in a manner that reduces the likelihood of the tine tips 146 puncturing the underside of the dermal layers 36. Preferably, the tine tips 146 are rounded bulbs or otherwise non-sharp so as to further protect the underside of the dermal layers 36. In alternative embodiments, the tines 145a-b may have a generally straight shape that extends substantially perpendicular to the longitudinal shaft portions of the anchors 140a-b to the rounds tips 146.

Still referring to FIGS. 2A-C, the retainer body 110 can include first and second retainer body portions 120a-b arranged on opposing sides of the longitudinal fold axis 160, retention posts 112a-b, left and right tabs 122a-b, and (optionally) a sloped nose region 130. The first and second retainer body portions 120a-b can be connected to each other at an elastically flexible web portion 150, which may be employed to define the fold axis 160.

The retainer body 110 can comprise one or more biocompatible polymer materials (e.g., PVC, polypropylene, polystyrene, or the like). In some embodiments, the retainer body 110 can comprise a combination of such materials, for example, when the flexible web portion comprises an elastically flexible silicone material while the first and second retainer body portions 120a-b comprise a less flexible polymer material such as polypropylene, PVC, polystyrene, or the like. In some embodiments, the retainer body 110 can be formed using a molding process in which the retainer body 110 is over-molded around a portion of the anchors 140a-b, especially in those embodiments in which the anchors 140a-b comprise a metallic material. For example, the left retainer body portion 120a can be over-molded around a portion of anchor 140a and, during the same or a different molding process, the right body portion 120b can be over-molded around a portion of anchor 140b. Consequently, as described further below, when the retainer body 110 is folded, the respective anchors 140a-b (being connected to the retainer body portions 120a-b respectively) likewise move in conjunction with their respective retainer body portion 120a-b.

Still referring to FIGS. 2A-C, the retention posts 112a-b can be configured to provide an effective coupling interface with a medical instrument 20, while providing features that simplify the overall use of the medical device anchor system 10. For example, in this embodiment, the retention posts 112a-b may provide the user with a simplified coupling technique for mating the anchor device 100 to the medical instrument 20, and may furthermore do so without the need for an attachable cap device or skin sutures. In the depicted example, the retention posts 112a-b in general are sized and spaced apart in a manner that is configured, for example, to be coupled with apertures 26a-b located on the wings 24a-b of the hub 22 of a catheter 20 (refer to FIG. 1). In this embodiment, the retention posts are substantially equally spaced from the longitudinal fold axis 160 of the retainer body 110. As described in more detail below, the retention posts 112a-b can include generally mushroom-shaped heads 114a-b, stem portions 116a-b, and relief portions 118a-b. In such circumstances, each of the retention posts 112a-b may have generally asymmetric shape about a vertical plane extending through a central vertical axis of each respective retention post 112a-b and extending generally parallel to the fold axis 160.

As described in more detail below, the shape and position of the retention posts 112a-b can permit a practitioner to intuitively mate the wings 24a-b of the catheter 20 (FIG. 1) with the retainer body 110 with the need for secondary locking mechanisms such a cap devices that attach to the retainer body 110, adhesive tapes, or the like. The mushroom-shaped heads 114a-b can have rounded tops that help the user align the apertures 26a-b with their respective retention posts 112a-b. In some embodiments, the mushroom-shaped heads 114a-b can be sized to have a low interference fit with the apertures 26a-b. For example, if the hub 22 of the medical device 20 can comprise an elastically flexible material, the user will be readily able to mate the hub 22 to the retention posts 112a-b of anchor device 100 by forcibly and temporarily flexing the apertures 26a-b over the mushroom-shaped heads 114a-b. Thus, when securing the medical device 20 to the anchor device 100, the user can align the apertures 26a-b with the mushroom-shaped heads 114a-b and lightly press the hub 22 of the medical device 20 against the anchor device 100 so that the apertures 26a-b pass over and below the mushroom-shaped heads 114a-b. The hub 22 can be pressed onto the anchor device by engaging one side at a time or by engaging both sides simultaneously. At that stage, the apertures 26a-b have passed over the mushroom-shaped heads 114a-b and surround the stem portions 116a-b of the retention posts 112a-b, thereby releasably securing the hub 22 of the medical instrument 20 in a position that is adjacent to the skin penetration point 32.

When the medical instrument 20 is installed on the anchor device 100, the apertures 26a-b are engaged with the stem portions 116a-b of the anchor device 100. The relative diameters of the apertures 26a-b and the stem portions 116a-b can advantageously provide for a slightly snug fit between the apertures 26a-b and the stem portions 116a-b. Such a snug fit can reduce the collection of contaminant materials between the apertures 26a-b and the stem portions 116a-b.

As will be described further below in reference to FIG. 6B, the flexibility of the wings 24a-b can allow some limited angular freedom of movement between the hub 22 and the anchor device 100, while generally restraining movement of the medical instrument 20 away from the skin penetration point 32. Further, the limited angular freedom of movement permits the hub 20 of the medical instrument 20 to be slightly tilted relative to the anchor device 100, thereby permitting the hub 20 and the distal portion 28 of the medical instrument to more closely align with the skin penetration point 32 and reduce the stresses applied by the medical instrument 20 at the skin penetration point 32.

Still referring to FIGS. 2A-C, the retention posts 112a-b can optionally include the aforementioned relief portions 118a-b. The relief portions 118a-b are generally planar or slightly curved surfaces on the sides of the retention posts 112a-b that act as material relief areas to make it easier to remove the wings 24a-b from retention posts 112a-b. In other words, the relief portions 118a-b can help the user decouple the medical instrument 20 from the anchor device 100. Specifically, the relief portions 118a-b can allow the user to slide their finger along the side of the anchor device 100, to better grasp the wings 24a-b between their thumb and forefinger, and to thereafter "peel" the wings 24a-b off the retention posts 112a-b. In some circumstances, the relief portions 118a-b can similarly facilitate the act of securing the wings 24a-b over the retention posts 112a-b.

Still referring to FIGS. 2A-2C, the anchor device 100 further includes first and second tabs 122a-b. The first and second tabs 122a-b are configured simplify the act of manipulating and folding the anchor device 100. For example, as described further in reference to FIGS. 3A-3B, the user can adjust the first and second tabs 122a-b in a pivoting motion toward one another, which readily enables the user to fold the anchor device 100 along the longitudinal fold axis 160. The first and second tabs 122a-b are also configured to provide a u-shaped cutout region 165 between the first and second tabs 122a-b. This u-shaped cutout region 165 can more readily provide visualization and access to the skin region under the retainer body 110 for inspection and cleaning of the skin 30 around the skin penetration point 32.

The anchor device 100 also includes a sloped nose region 130. The sloped nose region 130 can be a generally planar surface near the distal end of the retainer body 110 that is oriented at a different angle than the generally planar surfaces of the first and second retainer body portions 120a-b. The sloped nose region 130 can decline from the generally planar surfaces of the first and second retainer body portions 120a-b such that the nose region 130 slopes downward in a distal direction towards longitudinal shafts 142a-b of the anchors 140a-b (e.g., and thus downward to the skin penetration point 32 when the anchor tines 145a-b are deployed). As will be described further in reference to FIG. 6B, the sloped nose region 130 can facilitate an orientation of the distal portion 28 of the medical instrument 20 that is directed toward the skin penetration point 32. In this manner, the stresses that can potentially be exerted on the skin 30 proximal to the skin penetration point 32 by the distal portion 28 of the medical instrument 20 can be reduced.

As shown in FIG. 2C, the flexible web portion 150 of the anchor device 100 can be positioned, for example, generally centrally between the first and second retainer body portions 120a-b. As previously described, the flexible web portion 150 can extend longitudinally from a distal face of the retainer body 110 to a proximal face of the retainer body 110, and can be used to define the fold axis 160 about which the first and second retainer body portions 120a-b are pivotable from the non-folded condition (FIG. 2A) to the folded condition (FIG. 3A). The left and right retainer body portions 120a-b can be connected opposing sides of the flexible web portion 150. The flexible web portion 150 can comprise an elastically flexible biocompatible polymer material (e.g., silicon, PVC, polypropylene, polystyrene, or the like). In some embodiments, the flexible web portion 150 can be made of the same material as the other portions of the retainer body 110. In other embodiments, the flexible web portion 150 can be made of a different material than the other portions of the retainer body 110. In such a case, the anchor device can be made, for example, using a two-step insert molding operation. The flexible web portion 150 can be biased to resiliently maintain the non-folded shape of the anchor device 100 as depicted in FIGS. 2A-2C. When the anchor device 100 is folded along the fold axis 160 due to a user's grasp (refer, for example to FIG. 4), the flexible web portion 150 can undergo elastic deformation such that flexible web potion 150 biases the anchor device 100 to return the non-folded condition (FIGS. 2A and 5) upon release from the user.

Referring now to FIGS. 3A-3B, in this example embodiment, the anchor device 100 may include features that allow the individual anchors 140a-b to be moved relative to each other so as to facilitate both insertion and removal of the anchor device 100 through the skin penetration point 32. For example, the anchor device 100 may have a foldable configuration in which a first portion of the retainer body 110 is pivotably coupled via a flexible hinge portion to a second portion of the retainer body 110.

More specifically, in this embodiment, the first retainer body portion 120a and the second retainer body portion 120b can be flexibly pivoted with respect to each other along a fold axis 160 extending longitudinally through the retainer body 110. To initiate the folding process of the anchor device 100, the user can apply a bending moment about the fold axis 160 to the first and second tabs 122a-b of the anchor device. Such a bending moment can cause an elastic deformation of the flexible web portion 150 so as to fold the anchor device along the fold axis 160 (refer to FIG. 3A). The first retainer body portion 120a can be fixedly coupled to the anchor 140a, and the second retainer body portion 120b can be fixedly coupled to the anchor 140b. Thus, as shown in FIG. 3A, when the first and second retainer body portions 120a-b are pivoted about the fold axis 160, the two anchors 140a-b likewise pivot relative to one another. This process of pivoting can cause the anchor device to transition from a non-folded condition (shown in FIGS. 2A-2C and in FIG. 1) in which the tines 145a-b extend generally away from one another to a folded condition (shown in FIGS. 3A-3B), in which the tines 145a-b are generally adjacent to each other and oriented to extend in substantially the same direction. Similarly, when the bending moment from the user is released, the anchor device can be biased to return the anchor device 100 from the folded condition to the non-folded condition. In the depicted embodiment, the tines 145a-b can be rotated about 75-degrees to about 105-degrees, and preferably about 90-degrees, during the transition between the non-folded condition and the folded condition. As described in more detail below, the anchor device 100 can be arranged in the folded condition during both insertion and removal of the subcutaneous tines 145a-b so as to reduce the likelihood of the tines 145a-b causing damage to the skin 30.

Figure 4:
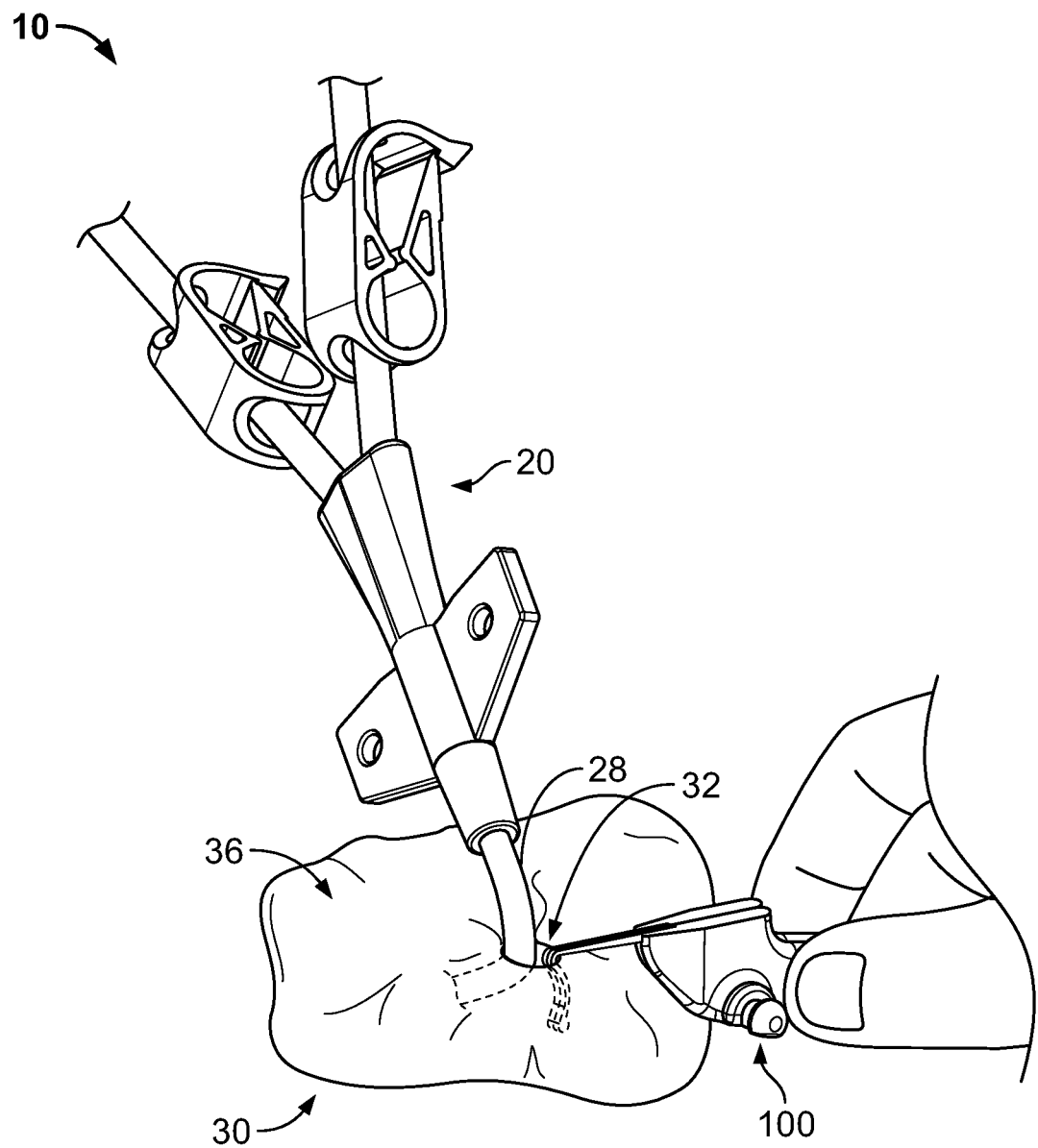
FIGS. 4, 5, and 6A-B are perspective views of an anchor system, including the anchor device of FIG. 1, for use in securing the position of a medical instrument.
Figure 5:
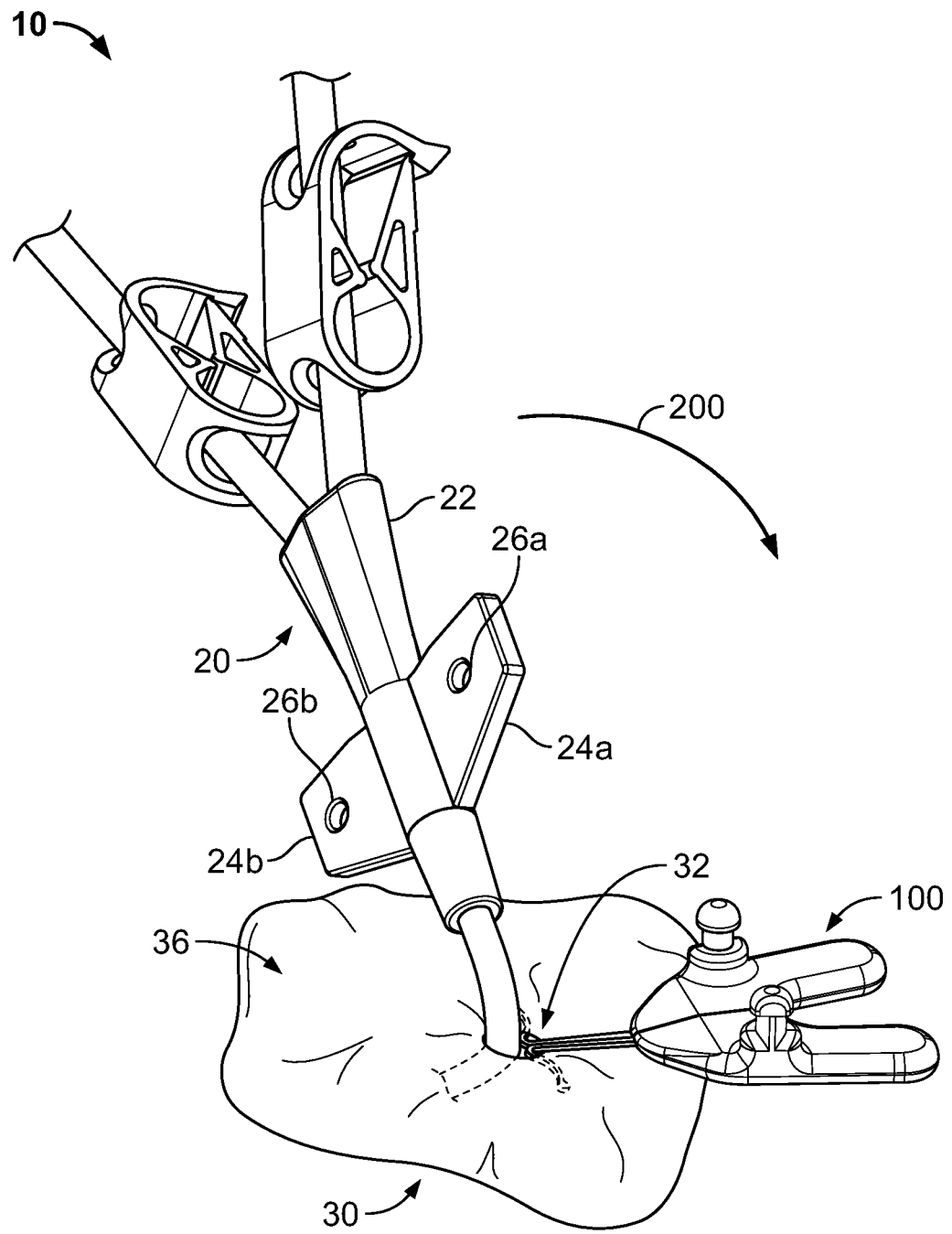

Referring now to FIGS. 4-5, in some embodiments, the medical instrument 20 can include a catheter to be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient.

After placement of the catheter 20 through the penetration point 32 of the skin 30, the user can grasp the anchor device 100 in the folded condition and approach the penetration point 32 such that the free ends of the tines 145a-b are contemporaneously inserted through the penetration point 32 while the tines 145a-b are in a generally side-by-side condition (as depicted in FIG. 4). In particular embodiments, the subcutaneous tines 145a-b are inserted through the skin penetration point 32 while the user conveniently grasps the tabs 122a-b of the retainer body 110 of the anchor device 100 and applies an insertion force until the convexly curved body portions of the subcutaneous tines 145a-b are positioned below the surface of the skin 30 (while the remainder of the anchor device 100 resides external to the skin 30).

As the anchor device 100 is inserted through the penetration point 32, the tines 145a-b are maintained in a generally non-stressed configuration (e.g., a first shape or a steady-state shape) while passing through the penetration point 32 in a manner that reduces the likelihood of trauma to the surrounding skin tissue 30. As the tines 145a-b are collectively advanced through the penetration point 32, the free ends of the tines 145a-b are moved beneath the dermal skin layers 36 of the skin 30.

When the tines 145a-b reach the subcutaneous region 34, the retainer body 110 can adjusted to the unfolded condition so that the tines 145a-b are shifted relative to one another, resulting in the tines 145a-b extending outwardly away from one another (as depicted in FIG. 5). During that process of unfolding the retainer body 110, each tine 145a-b may retain their generally non-stressed configuration (e.g., the first shape or the steady-state shape). Thus, the anchor device 100 can be installed in accordance with a technique that reduces or eliminates the need to shift the subcutaneous anchors tines 145a-b to or from a flexed or stressed configuration during the passage through the skin penetration point 32. As such, the subcutaneous anchors tines 145a-b need not undergo substantial flexing during installation or removal, and in some embodiments, the subcutaneous anchors tines 145a-b can comprise a generally less costly material (such as stainless steel or biocompatible polymers) rather than more costly materials required for superelastic flexing.

As previously described, the retainer body 110 can secure the medical instrument 20 relative to a skin penetration point 32. With the anchor device 100 positioned such that subcutaneous anchors tines 145a-b are in their deployed configuration, as shown in FIG. 5, the previously inserted medical instrument 20 can be releasably secured to the anchor device 100. As shown in FIG. 5, the directional arrow 200 depicts an example motion of manually positioning the medical instrument 20 adjacent to the anchor device 100 to prepare for the installation of the medical instrument 20 onto the anchor device 100.

Figure 6A:
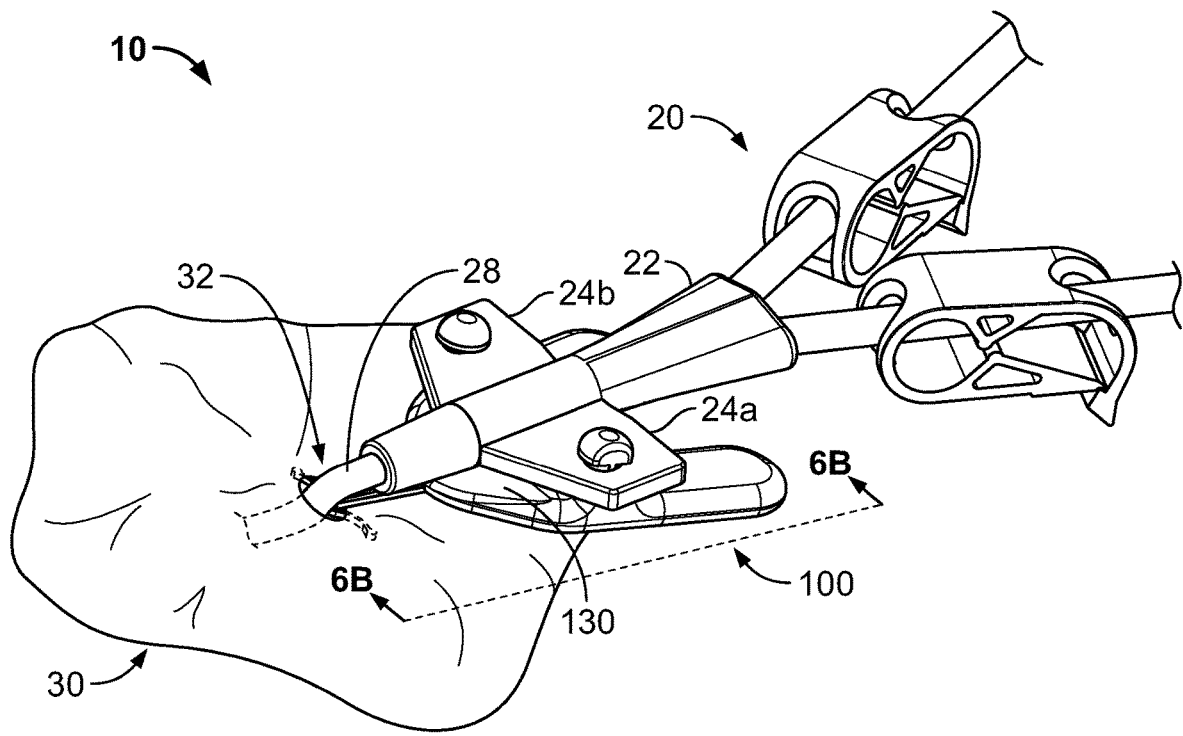
Figure 6B:
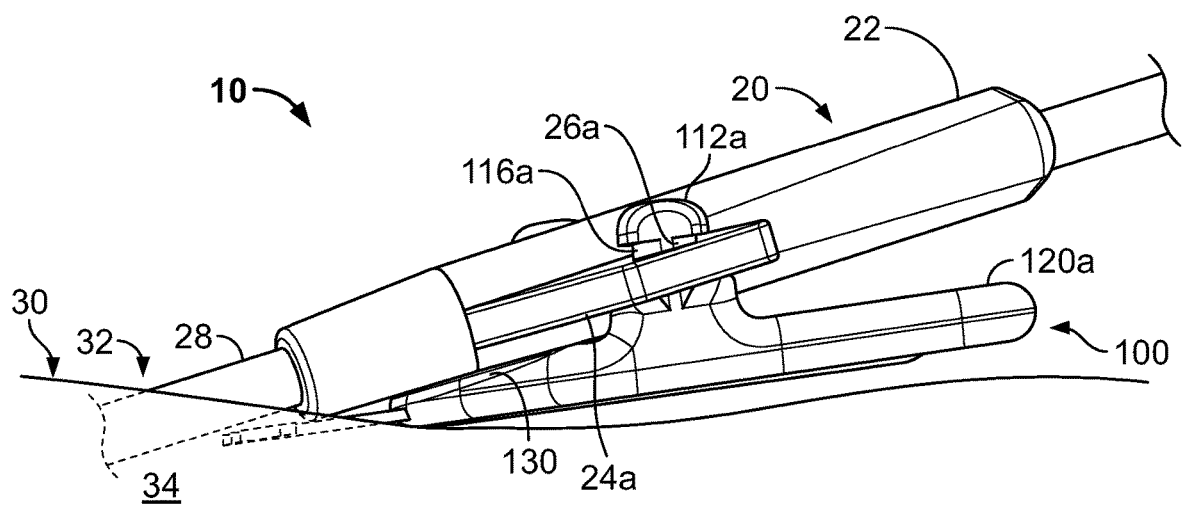

Referring now to FIGS. 6A-B, the medical device anchor system 10 of FIGS. 4-5 is releasably engaged with the medical instrument 20. In this embodiment, the hub 22 of the medical instrument 20 (e.g., a catheter) may be removably attached to the retainer body 110 using one or more apertures 26a-b on the wings 24a-b of the hub 22 that mechanically engage with corresponding retention posts 112a-b on the retainer body 110. To simplify the process of engaging the apertures 26a-b with the retention posts 112a-b, the hub 22 may comprise an elastically flexible material, such as silicone or another biocompatible polymer material. Such flexibility can assist the user to install the medical instrument 20 onto the anchor device 100 by making it possible to bend, stretch, and generally make it easy to maneuver the wings 24a-b of the hub 22 that comprise the apertures 26a-b. In some embodiments, at least a flexible wall portion comprising the wings 24a-b may comprise silicone or another biocompatible polymer material so that left wing 24a can flexibly adjust relative to a right wing 24b, or at least to the barrel of the hub 22. In some embodiments, the hub 22 can comprise a composite material. That is, the wings 24a-b may comprise silicone or another flexible polymer material, while the other portions of the hub 22 may comprise a more rigid material such as a polycarbonate, PVC, or the like. In such circumstances, the apertures 26a-b can be aligned with and forced over the corresponding retention posts 112a-b, and thereafter (if desired), one aperture 26a or 26b can be lifted from the retainer body 110 while the second aperture 26b or 26a remains secured to the retainer body 110. With the apertures 26a-b coupled with the retention posts 112a-b, the medical instrument 20 is installed on the anchor device 100.

As shown in FIG. 6B, the anchor device 100 releasably retains the medical instrument 20 (e.g., catheter) in an operative position relative to a portion of skin 30 (e.g., the skin penetration point 32). The medical instrument 20 is mechanically coupled to the anchor device 100, as described above. The anchor device 100, in turn, is coupled to the portion of skin 30, as described above. In such embodiments, the anchor device 100 can be secured to the patient without necessarily requiring sutures or adhesive tapes bonded to the skin 30. A distal portion 28 of the catheter 20 penetrates a skin penetration point 32 and distally extends into the subcutaneous layer 34. In this view, it can be seen that some embodiments of the system 10 can enable the distal end of the hub 22 to be positioned closely to the skin penetration point 32. Such a configuration provides a compact anchor system 10 that is convenient to install and maintain. This configuration can minimize the lengths of the tubing proximal to the patient, and reduce the need for securement of such tubing or other portions of the medical instrument 20 to the patient using tapes, adhesive dressings, and the like.

It can also be seen in FIG. 6B that the hub 22 of the catheter 20 may optionally inclined at an angle in relation to the skin surface 30. Such an orientation between the hub 22 and the skin 30 may, in some circumstances, reduce the stresses applied to the skin penetration point 32 of the patient by the distal portion 28 of the catheter 20. In particular, the example orientation depicted in FIG. 6B enables the distal portion 28 to be inclined at an angle in relation to the skin surface 30 which can thereby reduce the need for the distal portion 28 of the catheter 20 to have the a significant bend at the skin penetration point.

Still referring to FIG. 6B, in some embodiments, the apertures 26a-b of the hub 22 can have a slidable fit in relation to the stems 116a-b of the retention posts 112a-b. The slidable fit relationship can provide the hub 22 with a freedom of movement whereby the distal portion 28 will tend to position itself in relation to the skin 30 so as to naturally minimize the amount of force applied by the distal portion 28 to the skin 30, and the sloped nose portion 130 of anchor device 100 can further allow the distal portion 28 to do so. For example, as described above in reference to FIGS. 2A-2C, the sloped nose region 130 can be a planar surface near the distal end of the retainer body 110 that is oriented at a different angle than the generally planar surfaces of the first and second portions 120a-b of the retainer body 110.

The sloped nose region 130 can be declined relative to the generally planar upper surfaces of the first and second portions 120a-b such that the sloped nose region 130 slopes downward in a distal direction towards the skin penetration point 32. Such a configuration of the anchor device 100 can allow the hub 22 of the catheter 20 to be further tilted at greater angle relative to the skin 30 and to the anchor device 100. The sloped nose region 130 can provide a material relief area that removes hindrances to the hub 22 from being positioned at an incline with relation to the skin. The sloped nose region 130 can also provide a planar surface to support the hub 22 in the inclined position in relation to the skin 30. Further, in some embodiments, the retention posts 112a-b can have their axes oriented at an angle generally perpendicular to the sloped nose region 130 (and thus non-perpendicular to the generally planar upper surfaces of the first and second portions 120a-b). In such a configuration, the retention posts 112a-b can encourage the hub 22 to be inclined in relation to the skin 30 because of the physical interface between the retention posts 112a-b and the apertures 26a-b of the hub 22.

In some embodiments, some components of the system 10 can be provided in a sterilized kit that pairs a particular type of catheter 20 or other medical instrument with a corresponding anchor device 100. The particular type of catheter 20 or other medical instruments in the kit is compatible for releasably mating with the retainer body 110 of the anchor device 100 in the kit. Each kit can include one or more anchor devices 100 and the particular type of catheter 20 or other medical instrument enclosed within a flexible packaging material, which preferably includes indicators that identify the type of catheter 20 or other medical instruments that is provided along with instructions for deploying and removing the anchor device 100. The kit may include a one-to-one ratio for the quantity of anchor devices 100 to the quantity of catheters 20. In other embodiments, the kit may include multiple anchor devices 100 (e.g., having differently sized or shaped tines 145a-b) for each catheter 20 contained therein.

Alternatively, in some embodiments, the anchor device 100 can be provided in individual, sterilized packets so that a practitioner can readily open such a packet and access the selected anchor device prior to insertion into the skin penetration point. Such individual packets can include a single anchor device enclosed within a flexible packaging material, which preferably includes indicators that identify the types of catheters or other medical instruments that are compatible for releasably mating with the retainer body 110. As such, a practitioner can readily select one of the packets for use after the type of catheter or medical instrument is selected for a particular patient.

Referring now to FIGS. 7A-C and 8, some embodiments of the anchor device 100 can be configured to operate in combination with an optional adapter tool 300, which permits the anchor device 100 to engage with a catheter 420 or other medical instrument even if no wings (or wings of a non-corresponding size) are provided. In such embodiments, the adapter tool 300 may be configured to engage and grip an exterior of the catheter 420 or other medical instrument while also providing supplemental wings 324a-b for mating with the retainer body 110 of the anchor device 100.

Figure 7A:
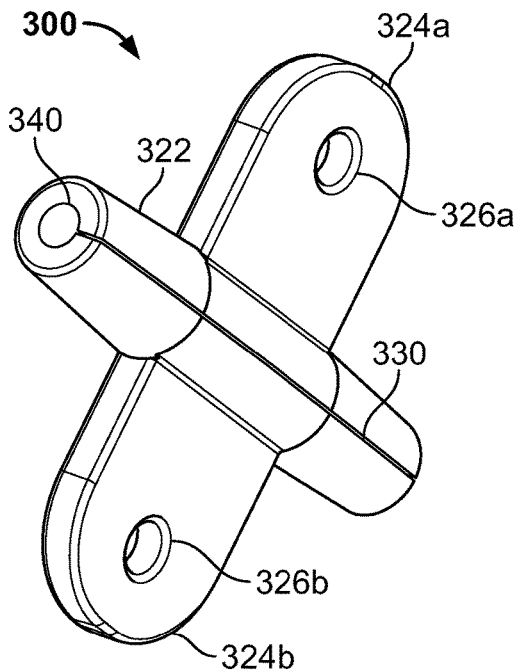
FIGS. 7A-7C are perspective views of shaft lock accessory for use with the anchor device of FIG. 1, for use in securing the position of a medical instrument.
Figure 7B:
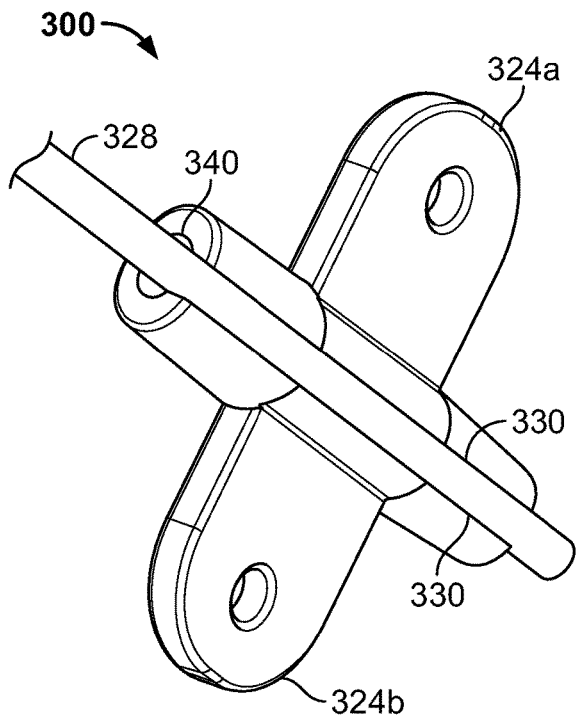
Figure 7C:
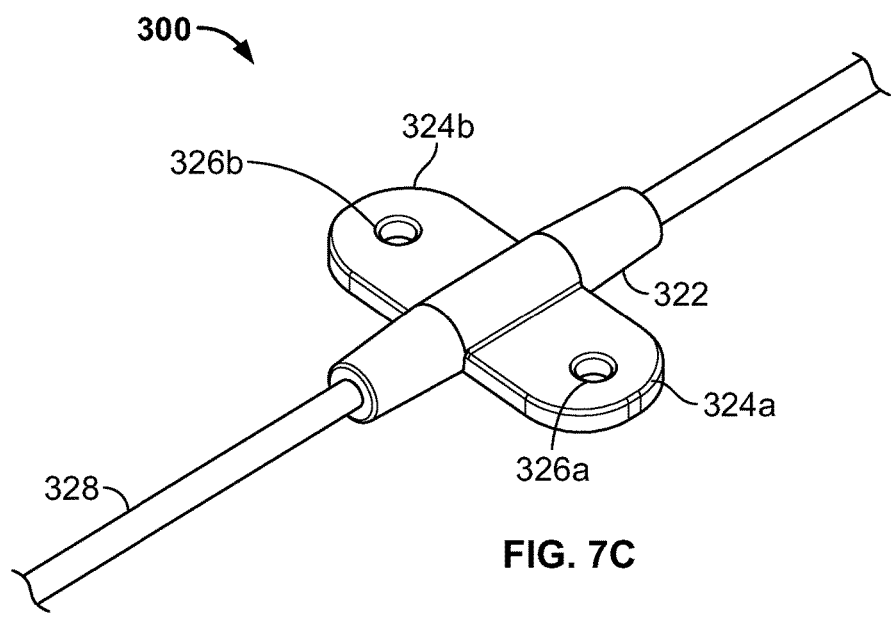

Referring FIGS. 7A-C, the adapter tool 300 can include a first portion 322 configured to releasably couple to a catheter or other medical instrument and a second portion 324a-b configured to releasably engage the retainer body 110 of the anchor device. In this embodiment, the first portion of the adapter tool 300 comprises a hub 322 that defines a lumen 340 with a longitudinal slit 330 through one wall of the hub 322. The longitudinal slit 330 can be flexibly opened to receive a medical instrument to be positioned within the lumen 340. In an example embodiment, the medical instrument can be a shaft 328 that is substantially surrounded by (and, in this embodiment, full surrounded by) the lumen 340 of the hub 322 of the adapter tool 300. To illustrate, FIG. 7A shows the adapter tool 300 without a medical instrument; FIG. 7B depicts the installation process of placing a medical instrument (e.g., a shaft 328 of a catheter or other medical instrument) into the lumen 340 of the adapter tool 300 by elastically deforming the hub 322 to widen the longitudinal slit 330; and FIG. 7C illustrates the shaft 328 installed in the adapter tool 300 such that the hub 322 fully surrounds and grips the exterior the shaft 328. In this configuration (as shown in FIG. 7C), the adapter tool 300 is prepared to be installed onto an anchor device 100.

The adapter tool 300 can comprise an elastically flexible biocompatible polymer material such as silicon, PVC, polypropylene, polystyrene, or the like. In some embodiments, the adapter tool 300 can comprise a composite strucutre. For example, the adapter tool 300 can have various layers of disparate materials. In some embodiments the adapter tool 300 can have a soft durometer material (e.g., an elastomeric material such as silicon) on the surface layer of the lumen 340 that contacts the medical instrument, and a stiffer polymer shell (e.g., polypropylene or PVC) on the upper layer (at least along the outer area of the hub 322). The softer inner layer can be bonded to a lower surface of the more rigid upper layer. Such a composite construction of the adapter tool 300 can provide sufficient frictional characteristics from the inner layer to grip the medical instrument inside of the lumen 340 while the upper layer of more rigid mater provide additional rigidity and maintains the compression of the inner layer upon the medical instrument. Further, in some embodiments the wings 324a-b can comprise the same material as the other portions of the adapter tool 300. In other embodiments, the wings 324a-b can comprise a different material than the other portions of the adapter tool 300, such that the wings 324a-b have more flexibility so as to make the installation of the adapter tool 300 to the anchor device more convenient.

Still referring to FIGS. 7A-C, in this embodiment, the second portion of the adapter tool 300 comprises wings 324a-b that extend laterally outward from opposing sides of the hub 322. The wings 324a-b of the adapter tool 300 can include apertures 326a-b. The apertures 326a-b can be configured to couple with retention posts of an anchor device, such as retention posts 112a-b of anchor device 100 as described above.

The adapter tool 300 can have a variety of styles of lumens 340 so as to adapt to various types of medical devices. For example, while the example embodiment of the adapter tool 300 shown has a lumen 340 with a circular cross-section, other configurations are envisioned, e.g., square, oval, or triangular cross-sections, and the like. In addition, various sizes of the lumen 340 are envisioned. For example, the lumen 340 can be sized to couple with tubes having various outer-diameter dimensions e.g., ¼", ³⁄₁₆", ⅛", ³⁄₃₂", ¹⁄₁₆", as well as other sizes including metric sizes.

In some embodiments, a plurality of the adapter tools 300 can be provided in a sterilized kit that provides adapters 300 having different shapes hubs 322 that are configured to mate with different types of catheter 20 or other medical instruments. Preferably, the plurality of the adapter tools 300 packaged together in the kit can include similar wing portions 324a-b such that any one of the plurality of the adapter tools 300 in the kit can be selected for mating with a predetermined retainer body 110 of the anchor device 100. Each kit can include plurality of the adapter tools 300 and, optionally, at least one of the particular types of anchor devices 100 enclosed within a flexible packaging material, which preferably includes indicators that identify the type of catheter 20 or other medical instruments that are compatible with the plurality of the adapter tools 300. The kit may include multiple adapters 300 (e.g., having differently sized or shaped hub portions 322) for each anchor device 100 contained therein. As such, a kit including multiple adapter tool 300 parts, with a range of different lumen sizes and/or shapes are envisioned. In another embodiment of a kit, a variety of the adapter tool 300 parts having different lumen sizes and/or shapes can be included with one or more anchor devices 100 designed to couple with the variety of adapter tool 300 parts. Such a kit can provide practitioners with a flexible system having the equipment to handle a variety of sizes and styles of medical instruments that can be anchored to a patient. In some embodiments, the kit, or individual parts comprising the kit, may be provided in sterile packaging.

Figure 8:
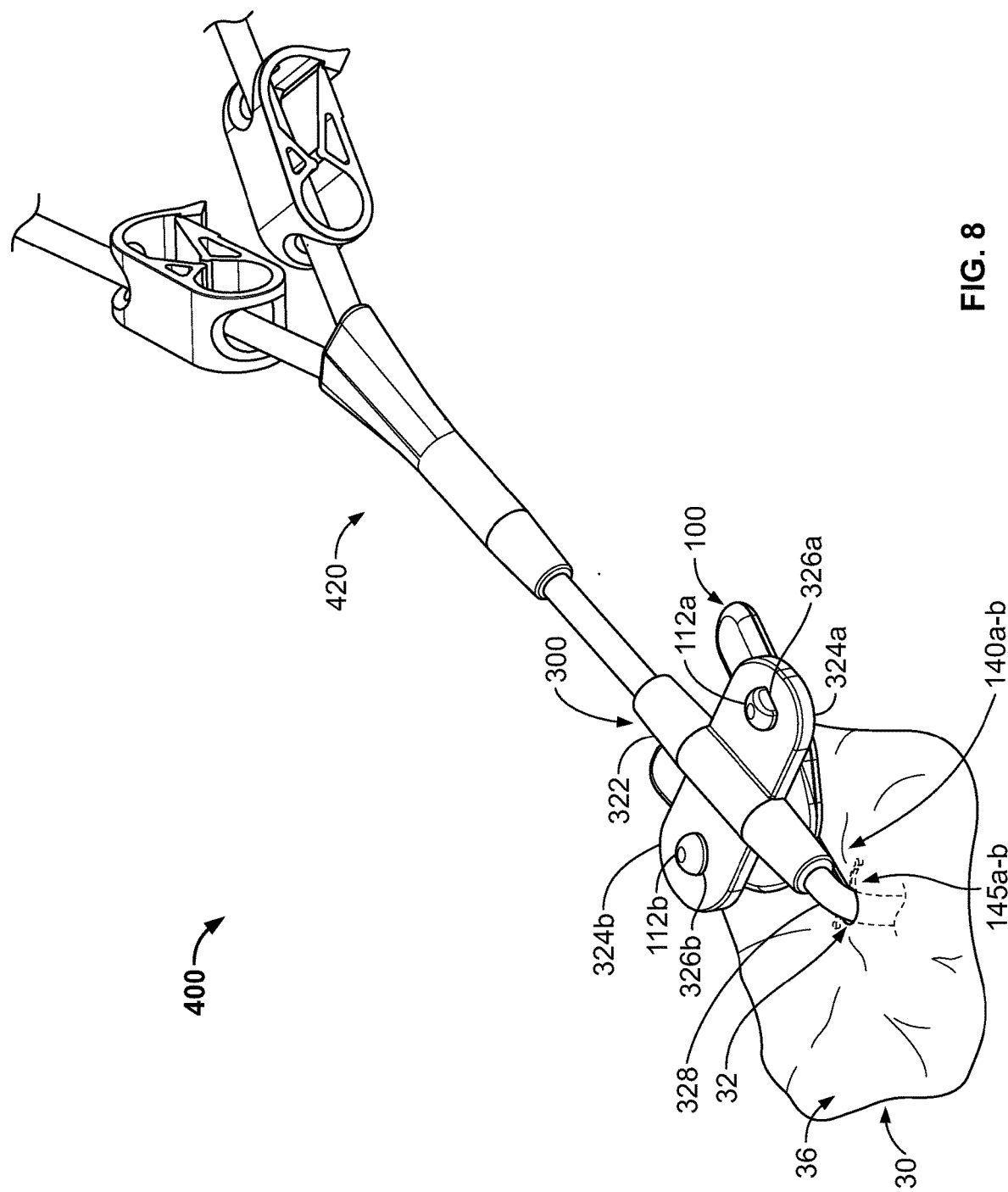
FIG. 8 is a perspective view of the anchor device of FIG. 1 coupled with the shaft lock accessory of FIGS. 7A-7C in a deployed configuration.

Referring now to FIG. 8, some embodiments of an example medical device anchor system 400 include an anchor device 100 coupled to an adapter tool 300 that releasably retains a medical instrument 420 in an operative position relative to a portion of skin 30 (e.g., skin penetration point 32). The medical instrument 420 can be mechanically coupled to the anchor device 100 by using the adapter tool 300, especially in circumstances when the medical instrument 420 is not equipped with corresponding wings (such as the wings 24a-b shown in FIG. 1). The anchor device 100, in turn, can be releasably anchored to the skin penetration point 32 as described, for example, in connection with FIGS. 4-5 herein. In this manner, the anchor device 100 and the adapter tool 300 can act as an intermediary members to bring about the retention of the medical instrument 420 in a desired position with respect to the skin penetration point 32.

In this embodiment, the distal portion 328 of the medical instrument 420 can be percutaneously delivered in the patient via the skin penetration point 32. The tines 145a-b of anchors 140a-b of anchor device 100 can be inserted through the skin penetration point 32 with the anchor device 100 in a folded configuration as described above in connection with FIG. 4. After insertion of the anchor tines 145a-b, the anchor device 100 can be adjusted to a non-folded configuration wherein the tines 145a-b of anchors 140a-b are extending outwardly away from one another under the dermal layers 36 of the patient, as described in connection with FIG. 5. The adapter tool 300 can be selected according to the type of the medical instrument 420 (e.g., based upon the diameter of the shaft 328 in this embodiments) and thereafter releasably installed on the distal portion 328 of the medical instrument 420, as described in connection with FIGS. 7A-C. The adapter tool 300 can be releasably secured onto the anchor device 100, for example, by pressing the wings 324a-b so that the apertures 326a-b are forced onto retention posts 112a-b, as in the manner described above. It should be understood that the adapter tool 300 can be oriented in relation to the anchor device 100 such that longitudinal slit 330 through one wall of the hub 322 faces downwardly toward the anchor device 100 and is adjacent to the anchor device 100, so that the medical instrument 420 can be securely retained in the adapter tool 300.

Figure 9:
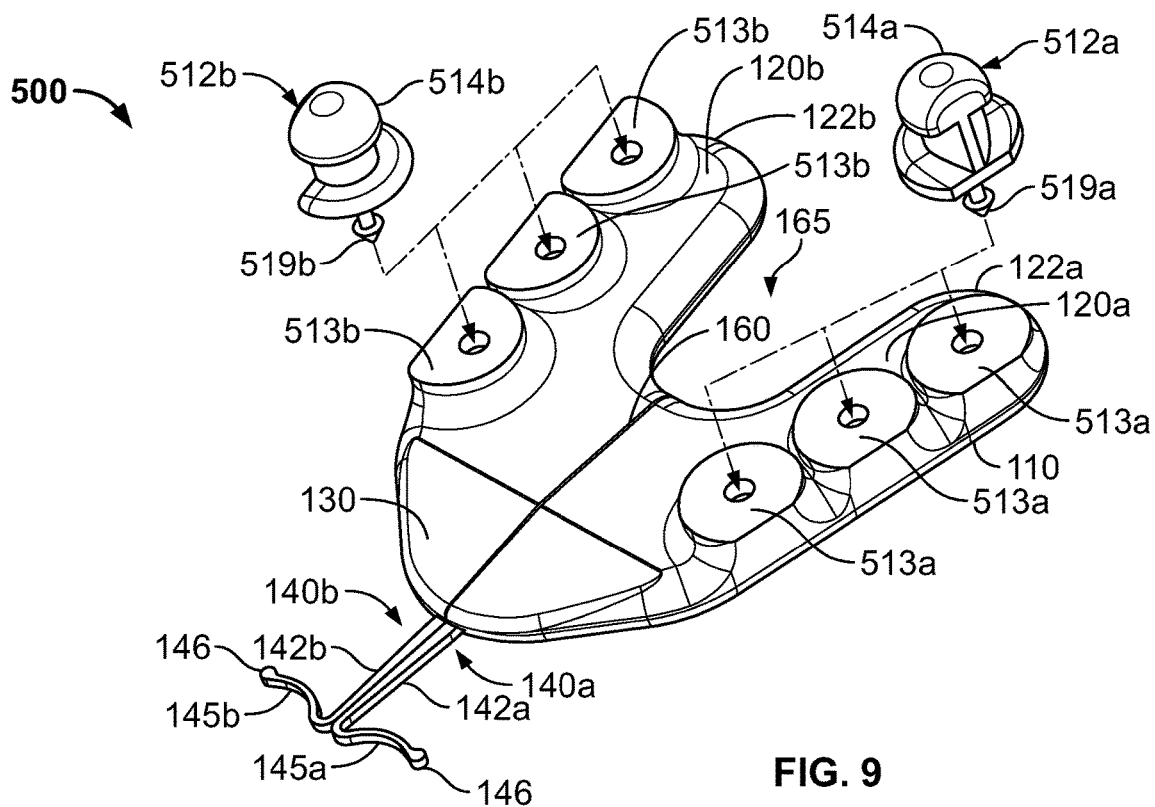
FIG. 9 is a perspective view of an anchor device in accordance with some alternative embodiments.

Referring now to FIG. 9, some alternative embodiments include an anchor device 500 in which the position of the retention posts can be adjusted relative to the retainer body. For example, the adjustable retention posts 512a-b can be selectively mounted at different positions relative to the retainer body 110, which can provide the capability for the user to select different dimensional distances between the retention posts. This feature can enable the anchor device to mate with any of a wider variety of medical instruments. That is, in some embodiments, the positions of the retention posts on the retainer body can be adjustable to accommodate coupling with a variety of medical instruments that have different sized mounting features (e.g., such as different catheters having differently shaped hubs/wings). For example, certain catheter hubs may have mounting features that have a different dimensional spacing in comparison to other catheter hubs. Having an anchor device with retention posts that can be adjusted to different dimensional spacing can enable the anchor device to mate with any of a variety of catheter hubs. This feature can also simplify the user's selection of anchor devices. In other words, since one anchor device can be adapted to a wider range of medical instruments, a single anchor device can be selected and configured in accordance with the mounting features of the medical instrument immediately before deployment.

The retainer body 110 of the example anchor device 500 depicted in FIG. 9 is substantially similar to the embodiments described above, but with the addition of multiple landings 513a-b along the upper face of the retainer body 110, so as to receive the adjustable retention posts 512a-b. Each landing 513a-b can include a mating structure to engage with a corresponding mating structure on the adjustable retention posts 512a-b respectively. For example, in some embodiments the landings 513a-b can have a mating cavity that lockingly receives corresponding projections 519a-b on the underside of the retention posts 512a-b (e.g., a snap-fit engagement). In other embodiments, the landings 513a-b can include threaded holes, and the corresponding projections 519a-b on the underside of the retention posts 512a-b can include male threads so that the retention posts 512a-b can be screwed onto the landings 513a-b.

Still referring to FIG. 9, in this embodiment, the landings 513a and 513b are configured in pairs. That is, each of the landings 513a on the first side has a corresponding landing 513b on the second side, and each of the landings 513b on the second side has a corresponding landing 513a on the first side. For example, the distal-most landing 513a on the left side of the anchor device 500, corresponds to the distal-most landing 513b on the right side of the anchor device 500. When, for example, the distal-most landing 513a on the left side is used to mount the adjustable retention post 512a, then the distal-most landing 513b on the right side can be used to mount the adjustable retention post 512b. This pattern holds true for the other less distally located landings 513a-b as well.

Each pair of landings 513a-b can be spaced apart from each other at a different distance in comparison to the other pairs of landings 513a-b. For instance, as depicted in the example embodiment shown in FIG. 9, the distal-most landings 513a-b can be a pair of landings 513a-b that are spaced the closest together (in comparison to the other pairs of landings 513a-b). In contrast, the pair of landings 513a-b located most proximally on the anchor device 500 can be a pair of landings 513a-b that are spaced the farthest apart (in comparison to the other pairs of landings 513a-b). The pairs between the distal-most and the most proximal can separated by distances that are between the closest and the farthest spacing distances. By selecting a suitable pair of landings 513a-b, and mounting the adjustable retention posts 512a-b to the suitable landings 513*a-b*, the anchor device 500 can be adjusted to accommodate a variety of medical instruments that have various sizes of mating structures. After the adjustable retention posts 512*a-b* are mated with the selected landings 513*a-b*, the anchor device 500 can operate in a manner substantially similar to the configuration described in connection with FIGS. 4-6B.

Figure 10:
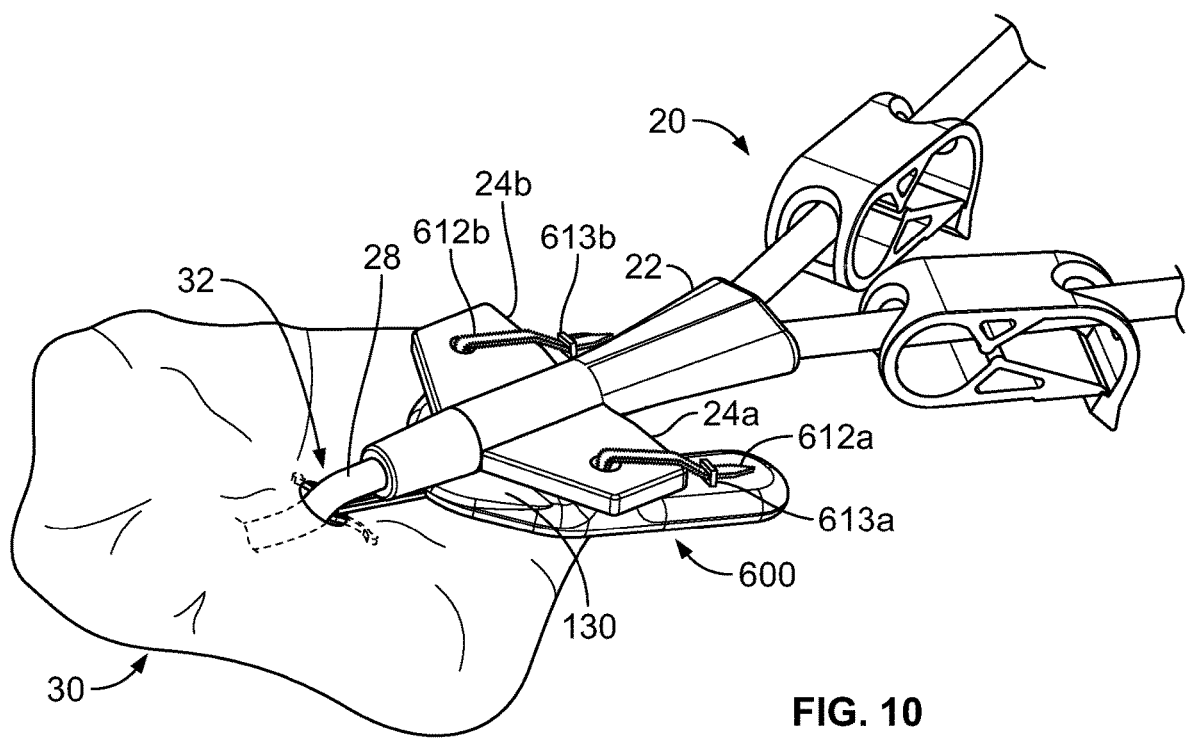
FIG. 10 is a perspective view of an anchor system, including an alternative embodiment of an anchor device.

Referring now to FIG. 10, some alternative embodiments of an anchor device 600 can be equipped with retention members that are flexible and therefore movable with respect to the retainer body. The flexible retention members 612*a-b* may have a different shape and configuration from the previously described retention posts 112*a-b* (FIGS. 2A-C). Such flexibility of the retention members 612*a-b* can enable the anchor device 600 to couple with any of a variety of medical instruments having a different of mounting interfaces. For example, while some medical instruments include wings with apertures, other medical instruments may be configured with a different type of mounting interface. Providing an anchor device 600 with flexible retention members 612*a-b* can enable the anchor device 600 to thereby couple with a wider variety of medical instruments. This feature can permit simplified user selection of anchor devices by providing a single anchor device 600 that is adaptable to a wider variety of medical instruments.

As shown in FIG. 10, in some embodiments, the flexible retention members 612*a-b* can comprise flexible binding straps, for example, having a structure somewhat similar to cable ties. The flexible retention members 612*a-b* can be fixedly attached to the upper face of the retainer body, for example by insert molding, welding, gluing, clamping, and so on. The elongate flexible portions of the flexible retention members 612*a-b* can be used to capture and secure the medical instrument 20. For example, as shown, in some embodiments the flexible retention members 612*a-b* can be routed through apertures located in the wings of a catheter hub. In other embodiments, the flexible retention members 612*a-b* can be routed so as to capture the medical instrument in many other manners—such as by routing the flexible retention members 612*a-b* over flanges or other outer surfaces, across outer surfaces in an "x" pattern, over individual tubes of a multi-tube device, and so on.

When the flexible retention members 612*a-b* are engaged with the medical instrument (e.g., routed through apertures located in the wings of a catheter hub in the depicted embodiment), the flexible retention members 612*a-b* can be firmly locked in place using a receiver locking device 613*a-b*. In some embodiments, the receiver locking device 613*a-b* can be a ratchet-type receiver mechanism that locks with a tooth surface along the side of the corresponding flexible retention member 612*a-b*. Such a configuration can allow the flexible retention members 612*a-b* to be pulled through the ratchet-type receiver mechanism 613*a-b* in one direction, which thereby locks the flexible retention members 612*a-b* tightly in place until the medical instrument 20 is released at the end of the procedure by unlocking or severing the retention members 612*a-b*. As shown in the example embodiment anchor device 600, the ratchet-type receiver mechanisms 613*a-b* can be fixedly mounted to the retainer body. To lock the medical instrument 20 in place on the anchor device 600, the free-ends of the flexible retention members 612*a-b* can be routed through the ratchet-type receiver mechanisms 613*a-b* and pulled tight. In this fashion a medical instrument can be coupled to an anchor device 600 using flexible retention members 612*a-b*.

In another embodiment, one flexible retention member (e.g., member 612*b*) can have a free-end with a pointed tip, while the other flexible retention member (e.g., 612*a*) can have a free-end with an integral ratchet-type receiver mechanism. Then, after interfacing the flexible retention members with the medical instrument, the two flexible retention members 612*a-b* can be joined together by routing the pointed tip through the ratchet-type receiver mechanism. The medical instrument can be secured to the anchor device by removing the slack from the flexible retention members. In this fashion a medical instrument can be coupled to an anchor device 600 using flexible retention members.

A number of embodiments of the invention have been described. Nevertheless, it will be understood that various modifications may be made without departing from the scope of the invention. Accordingly, other embodiments are within the scope of the following claims.

What is claimed is:

1. An anchor device for securing the position of a medical instrument, the anchor device comprising:
a retainer body comprising a first body portion that includes a first tab and a second body portion that includes a second tab; and
first and second anchors that extend distally from a distal end of the retainer body, each anchor comprising a flexible tine that is deployable in a subcutaneous region to secure the retainer body relative to a penetration point, the first anchor being coupled to the first body portion and the second anchor being coupled to the second body portion,
wherein the first body portion of the retainer body is adjustable relative to the second body portion so that the first and second anchors are adjustable from a first configuration to a second configuration; and
wherein the first tab of the first body portion and the second tab of the second body portions define a cutout region therebetween at a proximal end opposite from the first and second anchors in the first configuration to provide visualization and access to a surface under the retainer body, and the first tab of the first body portion is adjacent to the second tab of the second body in the second configuration.

2. The anchor device of claim 1, wherein the first tab is symmetrical with the second tab.

3. The anchor device of claim 1, wherein the cutout region defined by the first and second tabs is a U-shaped cutout region.

4. The anchor device of claim 1, wherein the first body portion is pivotably coupled to the second body portion about a longitudinal fold axis.

5. The anchor device of claim 4, wherein the first body portion of the retainer body is pivotable relative to the second body portion about the longitudinal fold axis so that the first and second anchors are adjustable from a first configuration in which the flexible tines extend outwardly away from one another to a second configuration in which the flexible tines extend generally in a same direction.

6. The anchor device of claim 5, wherein the retainer body comprises one or more anchor engagement portions configured to releasably receive one or more corresponding apertures defined by a hub of a catheter.

7. The anchor device of claim 6, wherein the one or more anchor engagement portions comprise one or more retention posts that extend upwardly from the retainer body.

8. The anchor device of claim 7, wherein the one or more retention posts extend from the retainer body at an angle that is generally transverse to the longitudinal fold axis.

9. The anchor device of claim 8, wherein the one or more retention posts are positioned along a perimeter of the retainer body.

10. The anchor device of claim 9, wherein the one or more retention posts comprise a first retention post extending upwardly from the retainer body on a first side of the longitudinal fold axis and a second retention post extending upwardly from the retainer body on a second side of the longitudinal fold axis.

11. The anchor device of claim 1, wherein the retainer body comprises a flexible web portion positioned generally centrally between the first and second body portions and extending longitudinally from the distal end of the retainer body to a proximal face of the retainer body, wherein the flexible web portion defines a longitudinal fold axis.

12. The anchor device of claim 11, wherein the flexible tines of the first and second anchors have a convex curvature facing towards the body portions.

13. The anchor device of claim 1, wherein the retainer body comprises a sloped nose region having a generally planar upper surface that is oriented at a decline angle extending distally from generally planar surfaces of the first and second body portions.

14. A system for securing the position of a medical instrument, the system comprising:
  an adapter including: a hub portion that is elastically deformable and configured to substantially surround and releasably engage with an outer surface of a medical instrument, and a second portion having one or more engagement members; and
  an anchor device comprising:
  a retainer body comprising a first body portion that includes a first tab and a second body portion that includes a second tab, and one or more anchor engagement portions configured to releasably couple with the one or more engagement members of the hub portion; and
  first and second anchors that extend distally from a distal end of the retainer body, each anchor comprising a flexible tine that is deployable in a subcutaneous region to secure the retainer body relative to a penetration point, the first anchor being coupled to the first body portion and the second anchor being coupled to the second body portion, wherein the first body portion of the retainer body is adjustable relative to the second body portion so that the first and second anchors are adjustable from a first configuration to a second configuration; and wherein the first tab of the first body portion and the second tab of the second body portions define a cutout region therebetween at a proximal end opposite from the first and second anchors in the first configuration to provide visualization and access to a surface under the retainer body, and the first tab of the first body portion is adjacent to the second tab of the second body in the second configuration.

15. The system of claim 14, wherein the hub portion of the adapter comprises a longitudinal slit that is configured to open to receive a portion of the medical instrument.

16. The system of claim 15, wherein the hub is configured to be tilted relative to the anchor device when the anchor engagement portions of the retainer body are engaged with the engagement members of the hub.

17. The system of claim 14, wherein the first tab is symmetrical with the second tab.

18. The system of claim 17, wherein the cutout region defined by the first and second tabs is a U-shaped cutout region.

19. The system of claim 18, wherein the first body portion is pivotably coupled to the second body portion about a longitudinal fold axis.

20. The system of claim 19, wherein the retainer body further comprises a sloped nose region having a generally planar upper surface that is oriented at a decline angle extending distally from generally planar surfaces of the first and second body portions.

* * * * *